US00PP30368P2

(12) United States Plant Patent
Verwer

(10) Patent No.: US PP30,368 P2
(45) Date of Patent: Apr. 9, 2019

(54) ***DAHLIA* PLANT NAMED 'DAHLGR152'**

(50) Latin Name: *Dahlia hybrida*
Varietal Denomination: Dahlgr152

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 15/732,492

(22) Filed: Nov. 20, 2017

(51) Int. Cl.
*A01H 5/02* (2018.01)

(52) U.S. Cl.
USPC ..... Plt./321

(58) Field of Classification Search
USPC ..... Plt./321
See application file for complete search history.

*Primary Examiner* — Keith O. Robinson
(74) *Attorney, Agent, or Firm* — C. A. Whealy

(57) ABSTRACT

A new and distinct cultivar of *Dahlia* plant named 'Dahlgr152', characterized by its upright, mounding and dense plant habit; freely basal branching habit; dark green-colored leaves; early and freely flowering habit; single-type inflorescence form; large inflorescences with light purple and white bi-colored ray florets; and good postproduction longevity and garden performance.

2 Drawing Sheets

Botanical designation: *Dahlia hybrida.*
Cultivar denomination: 'DAHLGR152'.

BACKGROUND OF THE INVENTION

The present invention relates to a new and distinct cultivar of *Dahlia* plant, botanically known as *Dahlia hybrida*, and hereinafter referred to by the name 'Dahlgr152'.

The new *Dahlia* plant is a product of a planned breeding program conducted by the Inventor in Lisse, The Netherlands. The objective of the breeding program is to create new compact container and garden *Dahlia* plants with dark-colored leaves, large single-type inflorescences and good postproduction longevity.

The new *Dahlia* plant originated from an open-pollination during the summer of 2013 of an unidentified seedling selection of *Dahlia hybrida*, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Lisse, The Netherlands during the summer of 2014.

Asexual reproduction of the new *Dahlia* plant by terminal cuttings since February, 2015 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dahlgr152'. These characteristics in combination distinguish 'Dahlgr152' as a new and distinct *Dahlia* plant:

1. Upright, mounding and dense plant habit.
2. Freely basal branching habit.
3. Dark green-colored leaves.
4. Early and freely flowering habit.
5. Single-type inflorescence form.
6. Large inflorescences with light purple and white bi-colored ray florets.
7. Good postproduction longevity and garden performance.

Plants of the new *Dahlia* differ primarily from plants of the female parent selection in the following characteristics:

1. Plants of the new *Dahlia* have larger inflorescences than plants of the female parent selection.
2. Plants of the new *Dahlia* are suitable as container and garden plants whereas plants of the female parent selection are suitable as garden plants.

Plants of the new *Dahlia* can be compared to plants of the *Dahlia hybrida* 'HDPI117', disclosed in U.S. Plant Pat. No. 23,279. In side-by-side comparisons, plants of the new *Dahlia* differ from plants of 'HDPI117' in the following characteristics:

1. Plants of the new *Dahlia* are taller and broader than plants of 'HDPI117'.
2. Leaves and leaflets of plants of the new *Dahlia* are more incised than leaves and leaflets of plants of 'HDPI117'.
3. Plants of the new *Dahlia* have larger inflorescences than plants of 'HDPI117'.
4. Plants of the new *Dahlia* and 'HDPI117' differ in ray floret color as plants of 'HDPI117' have light purple and light pink bi-colored ray florets.

Plants of the new *Dahlia* can also be compared to plants of the *Dahlia hybrida* 'HS Wink', disclosed in U.S. Plant Pat. No. 18,424. In side-by-side comparisons, plants of the new *Dahlia* differ from plants of 'HS Wink' in the following characteristics:

1. Plants of the new *Dahlia* are shorter and narrower than plants of 'HS Wink'.
2. Leaves and leaflets of plants of the new *Dahlia* are more incised than leaves and leaflets of plants of 'HS Wink'.
3. Plants of the new *Dahlia* start flowering about ten days later than plants of 'HS Wink'.
4. Plants of the new *Dahlia* have larger inflorescences than plants of 'HS Wink'.
5. Plants of the new *Dahlia* and 'HS Wink' differed in ray floret color as plants of 'HS Wink' have light purple and red purple bi-colored ray florets.
6. Plants of the new *Dahlia* are suitable as container and garden plants whereas plants of 'HS Wink' are suitable as garden plants.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Dahlgr152' grown in an outdoor nursery.

The photograph on the second sheet is a close-up view of typical inflorescences of 'Dahlgr152'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 15° C. to 30° C. and night temperatures ranged from 10° C. to 20° C. Plants were pinched one time about two to three weeks after planting. Plants were three months old when the photographs were taken and four months old when the description was taken. In the following description, color references are made to The Royal Horticultural Society Colour Chart, 1995 Edition, except where general terms of ordinary dictionary significance are used.

Botanical classification: *Dahlia hybrida* 'Dahlgr152'.

Parentage:

*Female, or seed, parent*.—Unidentified seedling selection of *Dahlia hybrida*, not patented.

*Male, or pollen, parent*.—Unknown selection of *Dahlia hybrida*, not patented.

Propagation:

*Type*.—By vegetative cuttings.

*Time to initiate roots, summer*.—About 12 days at soil temperatures about 15° C. and air temperatures ranging from about 15° C. to 25° C.

*Time to initiate roots, winter*.—About 13 to 14 days at soil temperatures about 15° C. and air temperatures ranging from about 15° C. to 25° C.

*Time to produce a rooted young plant, summer*.—About 20 days at soil temperatures about 15° C. and air temperatures ranging from about 20° C. to 25° C.

*Time to produce a rooted young plant, winter*.—About 21 days at soil temperatures about 15° C. and air temperatures ranging from about 20° C. to 25° C.

*Root description*.—Fine, fleshy.

*Rooting habit*.—Moderately freely branching; dense.

*Tubers*.—Length: About 16 cm. Diameter: About 15 cm. Texture: Corky. Color: Typically white to brown in color, actual color of the roots is dependent on substrate composition, water quality, fertilizer type and formulation, substrate temperature and physiological age of roots.

Plant description:

*Plant and growth habit*.—Upright and mounding plant habit; suitable as container and garden plants; inverted triangular plant form; freely basal branching with about six to seven primary lateral branches developing per plant each with about four secondary lateral branches; dense and bushy appearance; inflorescences held above the foliar plane on strong peduncles; vigorous growth habit.

*Plant height, soil level to top of foliar plane*.—About 55 cm.

*Plant height, soil level to top of floral plane*.—About 60 cm.

*Plant diameter or spread*.—About 35 cm.

*Lateral branches*.—Length: About 15 cm to 35 cm. Diameter: About 6 mm to 12 mm. Internode length: About 4 cm to 12 cm. Texture and luster: Smooth, glabrous; semi-glossy. Strength: Strong. Aspect: Erect to outwardly. Color: Close to 146A; distally tinged with close to 187A.

Leaf description:

*Arrangement*.—Opposite, simple or compound with three or five leaflets per leaf.

*Leaf length, simple leaves*.—About 23 cm.

*Leaf width, simple leaves*.—About 16 cm.

*Leaflet length*.—About 6 cm.

*Leaflet width*.—About 3 cm.

*Shape, simple leaves or leaflets*.—Ovate.

*Apex, simple leaves or leaflets*.—Aristulate.

*Base, simple leaves or leaflets*.—Attenuate.

*Margin, simple leaves or leaflets*.—Serrate; sinuses medium in depth and divergent.

*Venation pattern, simple leaves or leaflets*.—Pinnate, reticulate.

*Texture and luster, upper surface, simple leaves or leaflets*.—Smooth, glabrous; semi-glossy.

*Texture and luster, lower surface, simple leaves or leaflets*.—Smooth, glabrous; matte.

*Color*.—Developing leaves or leaflets, upper surface: Somewhat darker than 139A. Developing leaves or leaflets, lower surface: Close to 191A. Fully expanded leaves or leaflets, upper surface: Close to 139A; venation, close to 139A. Fully expanded leaves or leaflets, lower surface: Close to 191A; venation, close to 187B.

*Petioles*.—Length, simple leaves or leaflets: About 6 cm. Diameter, simple leaves or leaflets: About 5 mm. Strength: Strong. Texture and luster, upper and lower surfaces, simple leaves or leaflets: Smooth, glabrous; matte. Color, simple leaves or leaflets, upper surface: Close to 187A. Color, simple leaves or leaflets, lower surface: Close to 200D.

Inflorescence description:

*Appearance and flowering habit*.—Single-type inflorescences with ray and disc florets developing acropetally on a receptacle; inflorescences positioned above and beyond the foliar plane on strong peduncles; inflorescences face upright to outwardly; freely flowering habit with typically more than 35 to 40 inflorescences developing per plant during the flowering season.

*Fragrance*.—None detected.

*Time to flower*.—Early flowering habit; plants begin flowering about 70 days after planting; flowering continuous during the late summer and autumn in The Netherlands.

*Post-production longevity*.—Good postproduction longevity; inflorescences maintain good substance for about ten to twelve days on the plant and for about four to five days as a cut flower; inflorescences persistent.

*Inflorescence buds*.—Height: About 2 cm. Diameter: About 1.8 cm. Shape: Oblate. Texture and luster: Smooth, glabrous; semi-glossy to glossy. Color: Mid-section, close to 178A; towards the apex, close to 71A; at the base, close to 147A.

*Inflorescence diameter*.—Large, about 10.8 cm.

*Inflorescence depth* (*height*).—About 2.3 cm.

*Disc diameter*.—About 2.6 cm.

*Receptacle height*.—About 2.4 cm.

*Receptacle diameter*.—About 2.4 cm.

*Receptacle color*.—Close to 146A.

*Ray florets*.—Number of ray florets per inflorescence: About eight arranged in a single whorl. Length: About 5.2 cm. Width: About 3.1 cm. Shape: Ovate, flat. Apex: Obtuse or mucronulate. Base: Attenuate. Margin: Entire. Aspect: Initially upright to roughly perpendicular to the peduncle. Texture and luster, upper surface: Smooth, glabrous; semi-glossy to velvety. Texture and luster, lower surface: Smooth, glabrous; matte. Color: When opening, upper surface: Close to 77A. When opening, lower surface: Close to 77A; at the base, close to 77B. Fully opened, upper surface: Distally, close to 75A; proximally, close to 155B; at the base, close to 14A; venation, similar to lamina colors; color does not change with development. Fully opened, lower surface: Close to 77B; towards the margins, close to 77C.

*Disc florets*.—Number of disc florets per inflorescence: About 120 arranged in about 18 whorls. Length: About 1.6 cm. Diameter: About 2 mm. Shape: Tubular; apex dentate, pentafid. Aspect: Mostly upright. Texture and luster: Smooth, glabrous; matte. Color: When opening, inner surface: Close to 185A. When opening, outer surface: Close to 2C. Fully opened, inner surface: Close to 15A; venation, close to 15A. Fully opened, outer surface: Close to 168B; venation, close to 168B.

*Phyllaries*.—Quantity per inflorescence: About five arranged in a single whorl. Length: About 1.5 cm. Width: About 5 mm. Shape: Ovate to lanceolate. Apex: Acute. Base: Attenuate. Margin: Entire. Texture and luster, upper surface: Smooth, glabrous; glossy. Texture and luster, lower surface: Smooth, glabrous; semi-glossy. Color, upper surface: Close to 200A. Color, lower surface: Close to 200B.

*Peduncles*.—Length, terminal peduncle: About 30 cm. Diameter, terminal peduncle: About 6 mm. Length, third peduncle: About 20 cm. Diameter, third peduncle: About 3 mm. Strength: Strong. Aspect: Mostly erect to 30° from vertical. Texture and luster: Smooth, glabrous; semi-glossy. Color: Close to 200B.

*Reproductive organs*.—Androecium, present on disc florets only: Quantity per disc floret: Five. Filament length: About 5 mm. Filament color: Close to 2B. Anther size: About 2 mm by less than 1 mm. Anther shape: Lanceolate. Anther color: Close to 17C. Pollen amount: Moderate. Pollen color: Close to 21A. Gynoecium, present on disc florets only: Quantity per floret: One. Stigma diameter: About 2 mm. Stigma shape: Lanceolate. Stigma color: Close to 11B. Style length: About 7 mm. Style color: Close to 1C. Ovary color: Close to 1D. Seeds: Seed development has not been observed on plants of the new *Dahlia* to date.

Disease & pest resistance: Plants of the new *Dahlia* have not been shown to be resistant to pathogens and pests common to *Dahlia* plants to date.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Dahlgr152' as illustrated and described.

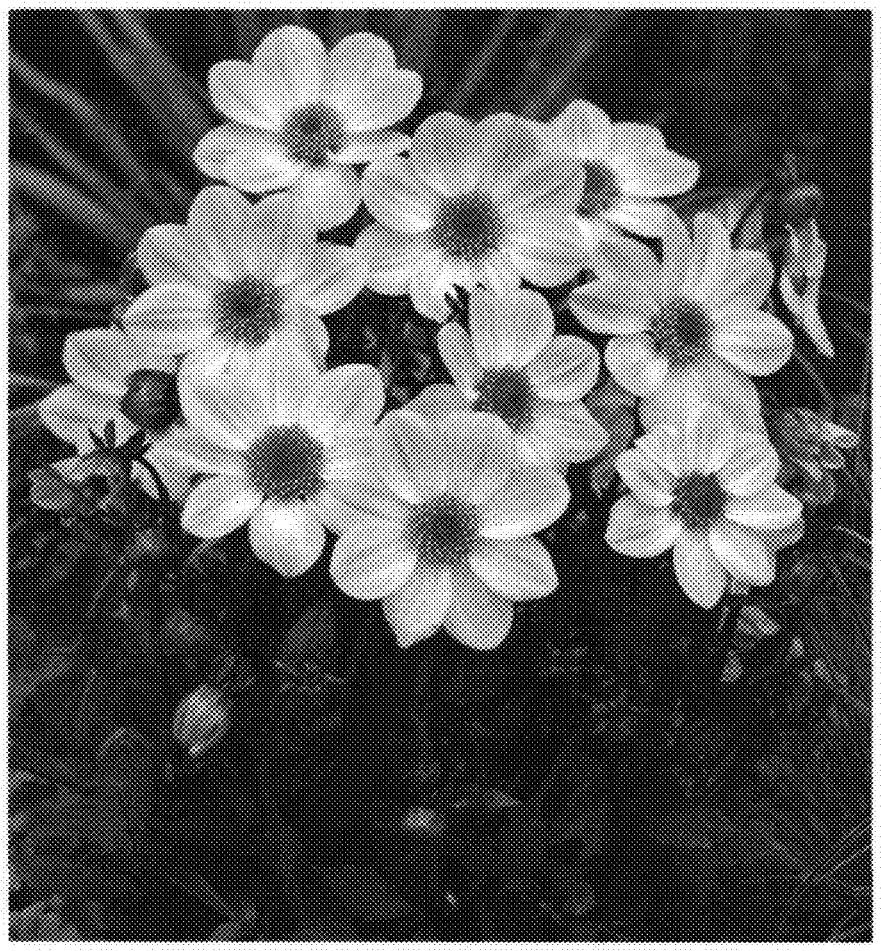

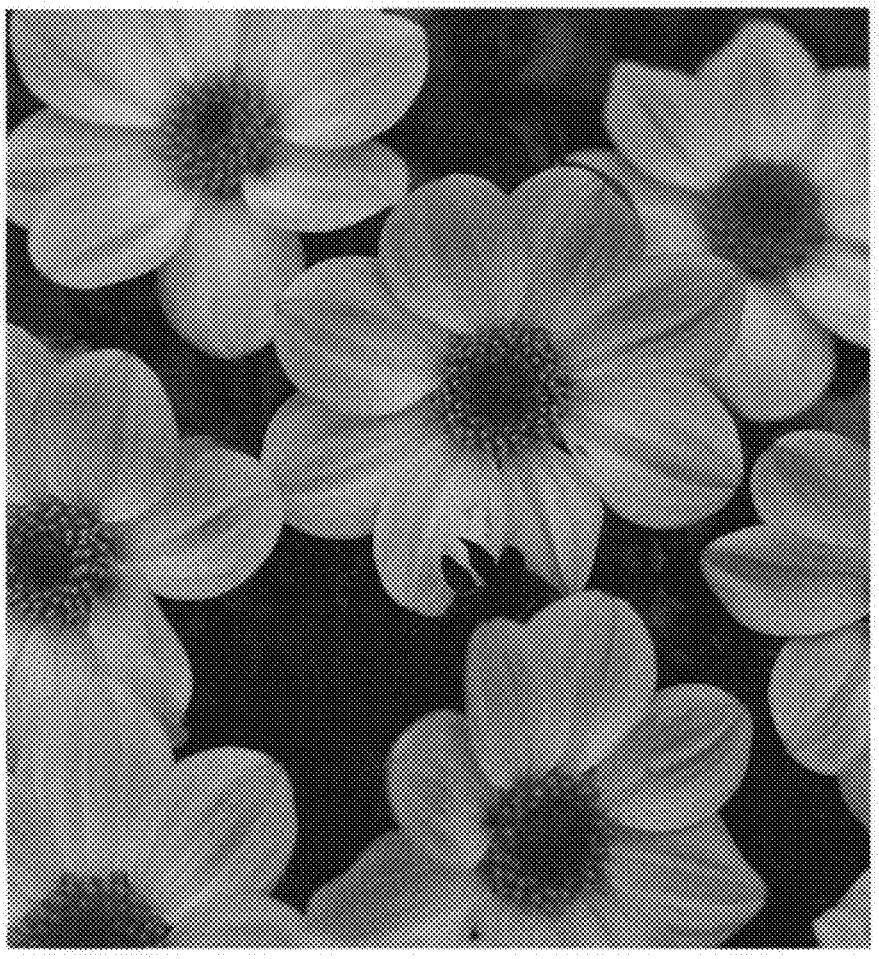

* * * * *